United States Patent [19]
Kerry-Williams et al.

[11] Patent Number: 5,965,386
[45] Date of Patent: Oct. 12, 1999

[54] YEAST STRAINS AND MODIFIED ALBUMINS

[75] Inventors: Sean Martin Kerry-Williams, Nottingham; Sarah Catherine Gilbert, Oxford, both of United Kingdom

[73] Assignee: Delta Biotechnology Limited, Nottingham, United Kingdom

[21] Appl. No.: 08/702,572

[22] PCT Filed: Mar. 1, 1995

[86] PCT No.: PCT/GB95/00434

§ 371 Date: Nov. 11, 1996

§ 102(e) Date: Nov. 11, 1996

[87] PCT Pub. No.: WO95/23857

PCT Pub. Date: Sep. 8, 1995

[30] Foreign Application Priority Data

Mar. 5, 1994 [GB] United Kingdom .................. 9404270

[51] Int. Cl.⁶ .................................................. C12N 15/00
[52] U.S. Cl. ..................................... 435/69.1; 435/254.21; 530/363; 536/23.1; 536/23.5
[58] Field of Search .................. 435/254.21, 23.1; 530/363; 536/23.1, 23.5

[56] References Cited

U.S. PATENT DOCUMENTS 5,440,018  8/1995  Ohmura et al. ......................... 530/363

FOREIGN PATENT DOCUMENTS 0329127    8/1989  European Pat. Off. .
0548012A1  6/1993  European Pat. Off. .

OTHER PUBLICATIONS

Egel–Mitani et al. (1990) Yeast. A Novel Aspartyl Protease Allowing Kex2–Independent MFalpha Propheromone Processing in Yeast. vol. 6:127–137, 1990.

Bourbonnais et al. (1991) Enzyme. Prohormone Processing by Yeast Proteases. vol. 45:244–256, 1991.

Lawn et al. (1981) Nucleic Acids Res. The Sequence of Human Serum Albumin cDNA and its Expression in E. coli. vol.9, No. 22, pp 6103–6114, 1981.

Kunkel (1985) Proc. Natl. Acad. Sci. USA Rapid and Efficient Site–Specific Mutagenesis Without Phenotypic Selection. vol.82:488–492, 1985.

Barton, "Protein Sequence Alignment and Database Scanning." In Protein Structure Prediction, A Practical Approach, 1996, IRL Press, Oxford University Press at Oxford, UK, pp. 31–63, 1996.

George et al. "Current Methods in Sequence Comparison and Analysis." In Macromolecular Sequencing and Synthesis, Selected Methods and Applications, 1988, D.H. Schlesinger (ed) Alan R. Liss, Inc. New York, NY, pp. 127–149, 1988.

Sleep et al. (1990) Bio/Technology 8:42–46, 1990.

Biochimie, vol. 76, 1994, pp. 226–233, Y. Bourbonnais et al., Cleavage of Prosomatostatins by The Yeast Yap3 and Kex2 Endoprotease.

Biotechnology, vol. 8, No. 1, 1990, pp. 42–46, D. Sleep et al., The Secretion of Human Serum Albumin from The Yeast S. Cerevisiae Using Five Different Leader Sequences.

Embo Journal, vol. 12, No. 1, 1993, pp. 285–294, Y. Bourbonnais et al., Isolation and Characterisation of S. Cerevisiae Mutants Defective in Somatostatin Expression . . .

Yeast, vol. 6, 1990, pp. 127–137, M. Egel–Mitani et al., A Novel Aspartyl Protease Allowing KEX2–Independent MF Alfa Propheromone Processing in Yeast.

Schwartz (1986) FEBS Lett. 200, 1–10.

Brenner et al (1992) Proc. Natl. Acad. Sci. 89, 922–26.

Zhu et al (1992) Mol. Microbiol. 6, 511–20.

*Primary Examiner*—Robert A. Wax
*Assistant Examiner*—Enrique D. Longton
*Attorney, Agent, or Firm*—Naomi S. Biswas

[57] ABSTRACT

Albumin, for example human albumin, is expressed and secreted in yeast which has been mutated to lack the yeast aspartyl protease 3 (Yap3p) or its equivalent, thereby reducing the production of a 45 kD albumin fragment. A further reduction is achieved by additionally deleting the Kex2p function. Alternatively, a modified albumin is prepared which is not susceptible to Yap3p cleavage, for example human albumin which is R410A, K413Q and K414Q.

27 Claims, 5 Drawing Sheets

SEQUENCE LISTING (1) GENERAL INFORMATION:

(iii) NUMBER OF SEQUENCES: 16

(2) INFORMATION FOR SEQ ID NO: 1:

(i) SEQUENCE CHARACTERISTICS:
        (A) LENGTH: 1830 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iii) ANTI-SENSE: NO (vi) ORIGINAL SOURCE:
        (A) ORGANISM: Homo sapiens (ix) FEATURE:
        (A) NAME/KEY: CDS
        (B) LOCATION: 73..1827

(xi) SEQUENCE DESCRIPTION: SEQ ID NO: 1:

ATGAAGTGGG TAAGCTTTAT TTCCCTTCTT TTTCTCTTTA GCTCGGCTTA TTCCAGGAGC        60

TTGGATAAAA GA GAT GCA CAC AAG AGT GAG GTT GCT CAT CGG TTT AAA         108

```
                Asp Ala His Lys Ser Glu Val Ala His Arg Phe Lys
                 1               5                  10

GAT TTG GGA GAA GAA AAT TTC AAA GCC TTG GTG TTG ATT GCC TTT GCT       156
Asp Leu Gly Glu Glu Asn Phe Lys Ala Leu Val Leu Ile Ala Phe Ala
         15              20                  25

CAG TAT CTT CAG CAG TGT CCA TTT GAA GAT CAT GTA AAA TTA GTG AAT       204
Gln Tyr Leu Gln Gln Cys Pro Phe Glu Asp His Val Lys Leu Val Asn
     30              35                  40

GAA GTA ACT GAA TTT GCA AAA ACA TGT GTT GCT GAT GAG TCA GCT GAA       252
Glu Val Thr Glu Phe Ala Lys Thr Cys Val Ala Asp Glu Ser Ala Glu
 45              50                  55                  60

AAT TGT GAC AAA TCA CTT CAT ACC CTT TTT GGA GAC AAA TTA TGC ACA       300
Asn Cys Asp Lys Ser Leu His Thr Leu Phe Gly Asp Lys Leu Cys Thr
                 65                  70                  75

GTT GCA ACT CTT CGT GAA ACC TAT GGT GAA ATG GCT GAC TGC TGT GCA       348
Val Ala Thr Leu Arg Glu Thr Tyr Gly Glu Met Ala Asp Cys Cys Ala
             80                  85                  90

AAA CAA GAA CCT GAG AGA AAT GAA TGC TTC TTG CAA CAC AAA GAT GAC       396
Lys Gln Glu Pro Glu Arg Asn Glu Cys Phe Leu Gln His Lys Asp Asp
         95                 100                 105

AAC CCA AAC CTC CCC CGA TTG GTG AGA CCA GAG GTT GAT GTG ATG TGC       444
Asn Pro Asn Leu Pro Arg Leu Val Arg Pro Glu Val Asp Val Met Cys
     110                 115                 120

ACT GCT TTT CAT GAC AAT GAA GAG ACA TTT TTG AAA AAA TAC TTA TAT       492
Thr Ala Phe His Asp Asn Glu Glu Thr Phe Leu Lys Lys Tyr Leu Tyr
125             130                 135                 140

GAA ATT GCC AGA AGA CAT CCT TAC TTT TAT GCC CCG GAA CTC CTT TTC       540
Glu Ile Ala Arg Arg His Pro Tyr Phe Tyr Ala Pro Glu Leu Leu Phe
             145                 150                 155

TTT GCT AAA AGG TAT AAA GCT GCT TTT ACA GAA TGT TGC CAA GCT GCT       588
Phe Ala Lys Arg Tyr Lys Ala Ala Phe Thr Glu Cys Cys Gln Ala Ala
         160                 165                 170

GAT AAA GCT GCC TGC CTG TTG CCA AAG CTC GAT GAA CTT CGG GAT GAA       636
Asp Lys Ala Ala Cys Leu Leu Pro Lys Leu Asp Glu Leu Arg Asp Glu
     175                 180                 185

GGG AAG GCT TCG TCT GCC AAA CAG AGA CTC AAG TGT GCC AGT CTC CAA       684
Gly Lys Ala Ser Ser Ala Lys Gln Arg Leu Lys Cys Ala Ser Leu Gln
 190                 195                 200

AAA TTT GGA GAA AGA GCT TTC AAA GCA TGG GCA GTA GCT CGC CTG AGC       732
Lys Phe Gly Glu Arg Ala Phe Lys Ala Trp Ala Val Ala Arg Leu Ser
205                 210                 215                 220

CAG AGA TTT CCC AAA GCT GAG TTT GCA GAA GTT TCC AAG TTA GTG ACA       780
Gln Arg Phe Pro Lys Ala Glu Phe Ala Glu Val Ser Lys Leu Val Thr
             225                 230                 235

GAT CTT ACC AAA GTC CAC ACG GAA TGC TGC CAT GGA GAT CTG CTT GAA       828
Asp Leu Thr Lys Val His Thr Glu Cys Cys His Gly Asp Leu Leu Glu
         240                 245                 250

TGT GCT GAT GAC AGG GCG GAC CTT GCC AAG TAT ATC TGT GAA AAT CAA       876
Cys Ala Asp Asp Arg Ala Asp Leu Ala Lys Tyr Ile Cys Glu Asn Gln
     255                 260                 265

GAT TCG ATC TCC AGT AAA CTG AAG GAA TGC TGT GAA AAA CCT CTG TTG       924
Asp Ser Ile Ser Ser Lys Leu Lys Glu Cys Cys Glu Lys Pro Leu Leu
 270                 275                 280

GAA AAA TCC CAC TGC ATT GCC GAA GTG GAA AAT GAT GAG ATG CCT GCT       972
Glu Lys Ser His Cys Ile Ala Glu Val Glu Asn Asp Glu Met Pro Ala
285                 290                 295                 300

GAC TTG CCT TCA TTA GCT GCT GAT TTT GTT GAA AGT AAG GAT GTT TGC      1020
Asp Leu Pro Ser Leu Ala Ala Asp Phe Val Glu Ser Lys Asp Val Cys
             305                 310                 315

AAA AAC TAT GCT GAG GCA AAG GAT GTC TTC CTG GGC ATG TTT TTG TAT      1068
```

```
                Lys Asn Tyr Ala Glu Ala Lys Asp Val Phe Leu Gly Met Phe Leu Tyr
                    320                 325                 330

GAA TAT GCA AGA AGG CAT CCT GAT TAC TCT GTC GTG CTG CTG CTG AGA           1116
Glu Tyr Ala Arg Arg His Pro Asp Tyr Ser Val Val Leu Leu Leu Arg
        335                 340                 345

CTT GCC AAG ACA TAT GAA ACC ACT CTA GAG AAG TGC TGT GCC GCT GCA           1164
Leu Ala Lys Thr Tyr Glu Thr Thr Leu Glu Lys Cys Cys Ala Ala Ala
350                 355                 360

GAT CCT CAT GAA TGC TAT GCC AAA GTG TTC GAT GAA TTT AAA CCT CTT           1212
Asp Pro His Glu Cys Tyr Ala Lys Val Phe Asp Glu Phe Lys Pro Leu
365                 370                 375                 380

GTG GAA GAG CCT CAG AAT TTA ATC AAA CAA AAT TGT GAG CTT TTT GAG           1260
Val Glu Glu Pro Gln Asn Leu Ile Lys Gln Asn Cys Glu Leu Phe Glu
                385                 390                 395

CAG CTT GGA GAG TAC AAA TTC CAG AAT GCG CTA TTA GTT CGT TAC ACC           1308
Gln Leu Gly Glu Tyr Lys Phe Gln Asn Ala Leu Leu Val Arg Tyr Thr
            400                 405                 410

AAG AAA GTA CCC CAA GTG TCA ACT CCA ACT CTT GTA GAG GTC TCA AGA           1356
Lys Lys Val Pro Gln Val Ser Thr Pro Thr Leu Val Glu Val Ser Arg
        415                 420                 425

AAC CTA GGA AAA GTG GGC AGC AAA TGT TGT AAA CAT CCT GAA GCA AAA           1404
Asn Leu Gly Lys Val Gly Ser Lys Cys Cys Lys His Pro Glu Ala Lys
    430                 435                 440

AGA ATG CCC TGT GCA GAA GAC TAT CTA TCC GTG GTC CTG AAC CAG TTA           1452
Arg Met Pro Cys Ala Glu Asp Tyr Leu Ser Val Val Leu Asn Gln Leu
445                 450                 455                 460

TGT GTG TTG CAT GAG AAA ACG CCA GTA AGT GAC AGA GTC ACC AAA TGC           1500
Cys Val Leu His Glu Lys Thr Pro Val Ser Asp Arg Val Thr Lys Cys
                465                 470                 475

TGC ACA GAA TCC TTG GTG AAC AGG CGA CCA TGC TTT TCA GCT CTG GAA           1548
Cys Thr Glu Ser Leu Val Asn Arg Arg Pro Cys Phe Ser Ala Leu Glu
            480                 485                 490

GTC GAT GAA ACA TAC GTT CCC AAA GAG TTT AAT GCT GAA ACA TTC ACC           1596
Val Asp Glu Thr Tyr Val Pro Lys Glu Phe Asn Ala Glu Thr Phe Thr
        495                 500                 505

TTC CAT GCA GAT ATA TGC ACA CTT TCT GAG AAG GAG AGA CAA ATC AAG           1644
Phe His Ala Asp Ile Cys Thr Leu Ser Glu Lys Glu Arg Gln Ile Lys
    510                 515                 520

AAA CAA ACT GCA CTT GTT GAG CTC GTG AAA CAC AAG CCC AAG GCA ACA           1692
Lys Gln Thr Ala Leu Val Glu Leu Val Lys His Lys Pro Lys Ala Thr
525                 530                 535                 540

AAA GAG CAA CTG AAA GCT GTT ATG GAT GAT TTC GCA GCT TTT GTA GAG           1740
Lys Glu Gln Leu Lys Ala Val Met Asp Asp Phe Ala Ala Phe Val Glu
                545                 550                 555

AAG TGC TGC AAG GCT GAC GAT AAG GAG ACC TGC TTT GCC GAG GAG GGT           1788
Lys Cys Cys Lys Ala Asp Asp Lys Glu Thr Cys Phe Ala Glu Glu Gly
            560                 565                 570

AAA AAA CTT GTT GCT GCA AGT CAA GCT GCC TTA GGC TTA TAA               1830
Lys Lys Leu Val Ala Ala Ser Gln Ala Ala Leu Gly Leu
        575                 580                 585

(2) INFORMATION FOR SEQ ID NO: 2:

(i) SEQUENCE CHARACTERISTICS:
        (A) LENGTH: 585 amino acids
        (B) TYPE: amino acid
        (D) TOPOLOGY: linear (ii) MOLECULE TYPE: protein (xi) SEQUENCE DESCRIPTION: SEQ ID NO: 2:

Asp Ala His Lys Ser Glu Val Ala His Arg Phe Lys Asp Leu Gly Glu
```

-continued

```
  1               5                   10                  15
Glu Asn Phe Lys Ala Leu Val Leu Ile Ala Phe Ala Gln Tyr Leu Gln
                20                  25                  30
Gln Cys Pro Phe Glu Asp His Val Lys Leu Val Asn Glu Val Thr Glu
                35                  40                  45
Phe Ala Lys Thr Cys Val Ala Asp Glu Ser Ala Glu Asn Cys Asp Lys
                50                  55                  60
Ser Leu His Thr Leu Phe Gly Asp Lys Leu Cys Thr Val Ala Thr Leu
 65                 70                  75                  80
Arg Glu Thr Tyr Gly Glu Met Ala Asp Cys Cys Ala Lys Gln Glu Pro
                    85                  90                  95
Glu Arg Asn Glu Cys Phe Leu Gln His Lys Asp Asp Asn Pro Asn Leu
                100                 105                 110
Pro Arg Leu Val Arg Pro Glu Val Asp Val Met Cys Thr Ala Phe His
                115                 120                 125
Asp Asn Glu Glu Thr Phe Leu Lys Lys Tyr Leu Tyr Glu Ile Ala Arg
130                 135                 140
Arg His Pro Tyr Phe Tyr Ala Pro Glu Leu Leu Phe Phe Ala Lys Arg
145                 150                 155                 160
Tyr Lys Ala Ala Phe Thr Glu Cys Cys Gln Ala Ala Asp Lys Ala Ala
                165                 170                 175
Cys Leu Leu Pro Lys Leu Asp Glu Leu Arg Asp Glu Gly Lys Ala Ser
                180                 185                 190
Ser Ala Lys Gln Arg Leu Lys Cys Ala Ser Leu Gln Lys Phe Gly Glu
                195                 200                 205
Arg Ala Phe Lys Ala Trp Ala Val Ala Arg Leu Ser Gln Arg Phe Pro
210                 215                 220
Lys Ala Glu Phe Ala Glu Val Ser Lys Leu Val Thr Asp Leu Thr Lys
225                 230                 235                 240
Val His Thr Glu Cys Cys His Gly Asp Leu Leu Glu Cys Ala Asp Asp
                245                 250                 255
Arg Ala Asp Leu Ala Lys Tyr Ile Cys Glu Asn Gln Asp Ser Ile Ser
                260                 265                 270
Ser Lys Leu Lys Glu Cys Cys Glu Lys Pro Leu Leu Glu Lys Ser His
                275                 280                 285
Cys Ile Ala Glu Val Glu Asn Asp Glu Met Pro Ala Asp Leu Pro Ser
290                 295                 300
Leu Ala Ala Asp Phe Val Glu Ser Lys Asp Val Cys Lys Asn Tyr Ala
305                 310                 315                 320
Glu Ala Lys Asp Val Phe Leu Gly Met Phe Leu Tyr Glu Tyr Ala Arg
                325                 330                 335
Arg His Pro Asp Tyr Ser Val Val Leu Leu Leu Arg Leu Ala Lys Thr
                340                 345                 350
Tyr Glu Thr Thr Leu Glu Lys Cys Cys Ala Ala Ala Asp Pro His Glu
                355                 360                 365
Cys Tyr Ala Lys Val Phe Asp Glu Phe Lys Pro Leu Val Glu Glu Pro
                370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
                405                 410                 415
Gln Val Ser Thr Pro Thr Leu Val Glu Val Ser Arg Asn Leu Gly Lys
                420                 425                 430
```

Val Gly Ser Lys Cys Cys Lys His Pro Glu Ala Lys Arg Met Pro Cys
        435                 440                 445

Ala Glu Asp Tyr Leu Ser Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
        530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

(2) INFORMATION FOR SEQ ID NO: 3:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (iii) ANTI-SENSE: NO (v) FRAGMENT TYPE: internal (xi) SEQUENCE DESCRIPTION: SEQ ID NO: 3:

Arg Tyr Thr Lys Lys
1               5

(2) INFORMATION FOR SEQ ID NO: 4:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (iii) ANTI-SENSE: NO (v) FRAGMENT TYPE: internal (xi) SEQUENCE DESCRIPTION: SEQ ID NO: 4:

Ala Tyr Thr Gln Gln
    1               5

(2) INFORMATION FOR SEQ ID NO: 5:

(i) SEQUENCE CHARACTERISTICS:
        (A) LENGTH: 39 base pairs
        (B) TYPE: nucleic acid (C) STRANDEDNESS: single
            (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 5:

CGTCAGACCT TGCATGCAGC CAAGACACCC TCACATAGC                              39

(2) INFORMATION FOR SEQ ID NO: 6:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iii) ANTI-SENSE: YES (xi) SEQUENCE DESCRIPTION: SEQ ID NO: 6:

CCGTTACGTT CTGTGGTGGC ATGCCCACTT CCAAGTCCAC CG                          42

(2) INFORMATION FOR SEQ ID NO: 7:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 7:

GCGTCTCATA GTGGAAAAGC TTCTAAATAC GACAACTTCC CC                          42

(2) INFORMATION FOR SEQ ID NO: 8:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iii) ANTI-SENSE: YES (xi) SEQUENCE DESCRIPTION: SEQ ID NO: 8:

CCCAAAATGG TACCTGTGTC ATCACTCGTT GGGATAATAC C                           41

(2) INFORMATION FOR SEQ ID NO: 9:

(i) SEQUENCE CHARACTERISTICS:
            (A) LENGTH: 44 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 9:

CCATCTGGAT CCAATGGTGC TTTGGCCAAA TAAATAGTTT CAGC                44

(2) INFORMATION FOR SEQ ID NO: 10:

(i) SEQUENCE CHARACTERISTICS:
          (A) LENGTH: 35 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iii) ANTI-SENSE: YES (xi) SEQUENCE DESCRIPTION: SEQ ID NO: 10:

GCTTCTTTTA CCGGTAACAA GCTTGAGTCC ATTGG                          35

(2) INFORMATION FOR SEQ ID NO: 11:

(i) SEQUENCE CHARACTERISTICS:
          (A) LENGTH: 37 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 11:

GGTAAGGTTT AGTCGACCTA TTTTTTGTTT TGTCTGC                        37

(2) INFORMATION FOR SEQ ID NO: 12:

(i) SEQUENCE CHARACTERISTICS:
          (A) LENGTH: 44 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iii) ANTI-SENSE: YES (xi) SEQUENCE DESCRIPTION: SEQ ID NO: 12:

GGAAACGTAT GAATTCGATA TCATTGATAC AGACTCTGAG TACG                44

(2) INFORMATION FOR SEQ ID NO: 13:

(i) SEQUENCE CHARACTERISTICS:
          (A) LENGTH: 24 amino acids
          (B) TYPE: amino acid
          (C) STRANDEDNESS: single
          (D) TOPOLOGY: linear (ii) MOLECULE TYPE: peptide (iii) HYPOTHETICAL: NO (iii) ANTI-SENSE: NO (v) FRAGMENT TYPE: N-terminal (xi) SEQUENCE DESCRIPTION: SEQ ID NO: 13:

Met Leu Leu Gln Ala Phe Leu Phe Leu Leu Ala Gly Phe Ala Ala Lys
1               5                  10                  15

Ile Ser Ala Asp Ala His Lys Ser
            20

(2) INFORMATION FOR SEQ ID NO: 14:

(i) SEQUENCE CHARACTERISTICS:
            (A) LENGTH: 4106 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iii) ANTI-SENSE: NO (vi) ORIGINAL SOURCE:
             (A) ORGANISM: Saccharomyces cerevisiae (xi) SEQUENCE DESCRIPTION: SEQ ID NO: 14:

| | | | | | |
|---|---|---|---|---|---|
| GAATTCTCTG | TTGACTACTA | AACTGAGAGA | ATTTGCCGAG | ACTCTAAGAA | CAGCTTTGAA | 60 |
| AGAGCGTTCT | GCCGATGATT | CCATAATTGT | CACTCTGAGA | GAGCAAATGC | AAAGAGAAAT | 120 |
| CTTCAGGTTG | ATGTCGTTGT | TCATGGACAT | ACCTCCAGTG | CAACCAAACG | AGCAATTCAC | 180 |
| TTGGGAATAC | GTTGACAAAG | ACAAGAAAAT | CCACACTATC | AAATCGACTC | CGTTAGAATT | 240 |
| TGCCTCCAAA | TACGCAAAAT | TGGACCCTTC | CACGCCAGTC | TCATTGATCA | ATGATCCAAG | 300 |
| ACACCATATG | GTAAATTAAT | TAAGATCGAT | CGTTTAGGAA | ACGTCCTTGG | CGGAGATGCC | 360 |
| GTGATTTACT | TAAATGTTGA | CAATGAAACA | CTATCTAAAT | TGGTTGTTAA | GAGATTACAA | 420 |
| AATAACAAAG | CTGTCTTTTT | TGGATCTCAC | ACTCCAAAGT | TCATGGACAA | GAAAACTGGT | 480 |
| GTCATGGATA | TTGAATTGTG | GAACTATCCT | GCCATGGCTA | TAATTTACCT | CAGCAAAAGG | 540 |
| CATCCGGTAT | TAGATACCAT | GAAAGTTTGA | TGACTCATGC | TATGTTGGAT | CACTGGCTGC | 600 |
| CACGTCGATG | AAACGTCTAA | ATTACCACTT | CGCTACCGTC | TGAAAATTCC | TGGGGTAAAG | 660 |
| ACTCCGGTAA | AGACGGATTA | TACGTGATGA | CTCAAAAGTA | CTTCGAGGAG | TACTGCTTTC | 720 |
| AAATTGTGGT | CGATATCAAT | GAATTGCCAA | AAGAGCTGGT | TCAAAATTC | ACCTCAGGTA | 780 |
| AGGAAGAGCC | GATTGTCTTG | CCCATCTGGA | CCCAATGGTG | CTTTGGCCAA | ATAAATAGTT | 840 |
| TCAGCAGCTC | TGATGTAGAT | ACACGTATCT | CGACATGTTT | TATTTTTACT | ATACATACAT | 900 |
| AAAAGAAATA | AAAAATGATA | ACGTGTATAT | TATTATTCAT | ATAATCAATG | AGGGTCATTT | 960 |
| TCTGAAACGC | AAAAAACGGT | AAATGGAAAA | AAAATAAAGA | TAGAAAAAGA | AAACAAACAA | 1020 |
| AGGAAAGGTT | AGCATATTAA | ATAACTGAGC | TGATACTTCA | ACAGCATCGC | TGAAGAGAAC | 1080 |
| AGTATTGAAA | CCGAAACATT | TTCTAAAGGC | AAACAAGGTA | CTCCATATTT | GCTGGACGTG | 1140 |
| TTCTTTCTCT | CGTTTCATAT | GCATAATTCT | GTCATAAGCC | TGTTCTTTTT | CCTGGCTTAA | 1200 |
| ACATCCCGTT | TTGTAAAAGA | GAAATCTATT | CCACATATTT | CATTCATTCG | GCTACCATAC | 1260 |
| TAAGGATAAA | CTAATCCCGT | TGTTTTTTGG | CCTCGTCACA | TAATTATAAA | CTACTAACCC | 1320 |
| ATTATCAGAT | GAAAGTGAGG | AAATATATTA | CTTTATGCTT | TTGGTGGGCC | TTTTCAACAT | 1380 |
| CCGCTCTTGT | ATCATCACAA | CAAATTCCAT | TGAAGGACCA | TACGTCACGA | CAGTATTTTG | 1440 |
| CTGTAGAAAG | CAATGAAACA | TTATCCCGCT | TGGAGGAAAT | GCATCCAAAT | TGGAAATATG | 1500 |

-continued

```
AACATGATGT TCGAGGGCTA CCAAACCATT ATGTTTTTTC AAAAGAGTTG CTAAAATTGG    1560

GCAAAAGATC ATCATTAGAA GAGTTACAGG GGGATAACAA CGACCACATA TTATCTGTCC    1620

ATGATTTATT CCCGCGTAAC GACCTATTTA AGAGACTACC GGTGCCTGCT CCACCAATGG    1680

ACTCAAGCTT GTTACCGGTA AAAGAAGCTG AGGATAAACT CAGCATAAAT GATCCGCTTT    1740

TTGAGAGGCA GTGGCACTTG GTCAATCCAA GTTTTCCTGG CAGTGATATA AATGTTCTTG    1800

ATCTGTGGTA CAATAATATT ACAGGCGCAG GGGTCGTGGC TGCCATTGTT GATGATGGCC    1860

TTGACTACGA AAATGAAGAC TTGAAGGATA ATTTTTGCGC TGAAGGTTCT TGGGATTTCA    1920

ACGACAATAC CAATTTACCT AAACCAAGAT TATCTGATGA CTACCATGGT ACGAGATGTG    1980

CAGGTGAAAT AGCTGCCAAA AAAGGTAACA ATTTTTGCGG TGTCGGGGTA GGTTACAACG    2040

CTAAAATCTC AGGCATAAGA ATCTTATCCG GTGATATCAC TACGGAAGAT GAAGCTGCGT    2100

CCTTGATTTA TGGTCTAGAC GTAAACGATA TATATTCATG CTCATGGGGT CCCGCTGATG    2160

ACGGAAGACA TTTACAAGGC CCTAGTGACC TGGTGAAAAA GGCTTTAGTA AAAGGTGTTA    2220

CTGAGGGAAG AGATTCCAAA GGAGCGATTT ACGTTTTTGC CAGTGGAAAT GGTGGAACTC    2280

GTGGTGATAA TTGCAATTAC GACGGCTATA CTAATTCCAT ATATTCTATT ACTATTGGGG    2340

CTATTGATCA CAAAGATCTA CATCCTCCTT ATTCCGAAGG TTGTTCCGCC GTCATGGCAG    2400

TCACGTATTC TTCAGGTTCA GGCGAATATA TTCATTCGAG TGATATCAAC GGCAGATGCA    2460

GTAATAGCCA CGGTGGAACG TCTGCGGCTG CTCCATTAGC TGCCGGTGTT TACACTTTGT    2520

TACTAGAAGC CAACCCAAAC CTAACTTGGA GAGACGTACA GTATTTATCA ATCTTGTCTG    2580

CGGTAGGGTT AGAAAAGAAC GCTGACGGAG ATTGGAGAGA TAGCGCCATG GGGAAGAAAT    2640

ACTCTCATCG CTATGGCTTT GGTAAAATCG ATGCCCATAA GTTAATTGAA ATGTCCAAGA    2700

CCTGGGAGAA TGTTAACGCA CAAACCTGGT TTTACCTGCC AACATTGTAT GTTTCCCAGT    2760

CCACAAACTC CACGGAAGAG ACATTAGAAT CCGTCATAAC CATATCAGAA AAAGTCTTC     2820

AAGATGCTAA CTTCAAGAGA ATTGAGCACG TCACGGTAAC TGTAGATATT GATACAGAAA    2880

TTAGGGGAAC TACGACTGTC GATTTAATAT CACCAGCGGG GATAATTTCA AACCTTGGCG    2940

TTGTAAGACC AAGAGATGTT TCATCAGAGG GATTCAAAGA CTGGACATTC ATGTCTGTAG    3000

CACATTGGGG TGAGAACGGC GTAGGTGATT GGAAAATCAA GGTTAAGACA ACAGAAAATG    3060

GACACAGGAT TGACTTCCAC AGTTGGAGGC TGAAGCTCTT TGGGGAATCC ATTGATTCAT    3120

CTAAAACAGA AACTTTCGTC TTTGGAAACG ATAAAGAGGA GGTTGAACCA GCTGCTACAG    3180

AAAGTACCGT ATCACAATAT TCTGCCAGTT CAACTTCTAT TTCCATCAGC GCTACTTCTA    3240

CATCTTCTAT CTCAATTGGT GTGGAAACGT CGGCCATTCC CCAAACGACT ACTGCGAGTA    3300

CCGATCCTGA TTCTGATCCA AACACTCCTA AAAAACTTTC CTCTCCTAGG CAAGCCATGC    3360

ATTATTTTTT AACAATATTT TTGATTGGCG CCACATTTTT GGTGTTATAC TTCATGTTTT    3420

TTATGAAATC AAGGAGAAGG ATCAGAAGGT CAAGAGCGGA AACGTATGAA TTCGATATCA    3480

TTGATACAGA CTCTGAGTAC GATTCTACTT TGGACAATGG AACTTCCGGA ATTACTGAGC    3540

CCGAAGAGGT TGAGGACTTC GATTTTGATT TGTCCGATGA AGACCATCTT GCAAGTTTGT    3600

CTTCATCAGA AAACGGTGAT GCTGAACATA CAATTGATAG TGTACTAACA AACGAAAATC    3660

CATTTAGTGA CCCTATAAAG CAAAAGTTCC CAAATGACGC CAACGCAGAA TCTGCTTCCA    3720

ATAAATTACA AGAATTACAG CCTGATGTTC CTCCATCTTC CGGACGATCG TGATTCGATA    3780

TGTACAGAAA GCTTCAAATT ACAAAATAGC ATTTTTTTCT TATAGATTAT AATACTCTCT    3840

CATACGTATA CGTATATGTG TATATGATAT ATAAACAAAC ATTAATATCC TATTCCTTCC    3900
```

```
GTTTGAAATC CCTATGATGT ACTTTGCATT GTTTGCACCC GCGAATAAAA TGAAAACTCC      3960

GAACCGATAT ATCAAGCACA TAAAAGGGGA GGGTCCAATT AATGCATATT TAAGACCACA      4020

GCTGAATAAC TTTAAAACGG CAGACAAAAC AAAAAATAGG TCGAATAAAC CTTACCTGCC      4080

TAGAAGGAAT GACAGCAGCT AATAAG                                          4106

(2) INFORMATION FOR SEQ ID NO: 15:

(i) SEQUENCE CHARACTERISTICS:
        (A) LENGTH: 2526 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Saccharomyces cerevisiae (xi) SEQUENCE DESCRIPTION: SEQ ID NO: 15:

CCGTTTTCTT TTCGTAAAAA AAAACAATAG ACACTATATA TAGACACTTT TTCCTTTCCT        60

TCTTTGCGCG ATTTCAAGAG GAAAAGCATA CTTAAATAAG AATATTCCTA AAACACACGT       120

TCTGACGCGT CAATTAGATC GTCAGACCTT GCATGCAGCC AAGACACCCT CACATAGCAC       180

TGCCTCCTTC CTCCTCTTTT CTGTCACCAC CTCACCTCCC TCGTCCACTC AACTGAGTGG       240

CTTTTCGCTC CTTTTATACT GCGCCATGAG TAGTTTTCGT TTCACTGATG TGTCCGAAAA       300

AATTGAGGTT TCATAAAAAA ATTCGTGGAC TTATTTATGG AGAAACAGGG AAATCCGACT       360

ACTTAAGAAA AGGGTGTCAA AGAGGATTTA CTTTTTTCCT TCTTTTTGCA TTTGTTCCTA       420

TTTCCGCAAT TGGACGGTTA TTAAGAAGAA CGCAATTGGC TTTTCTGTAT ATTAAAATAC       480

ATAGCGTAAT AAAAAGATAA GGTGAACACC AAGCATATAG TATAATATTA CCTACCACAT       540

ATGAAACTGA AAACTGTAAG ATCTGCGGTC CTTTCGTCAC TCTTTGCATC GCAGGTTCTC       600

GGTAAGATAA TACCAGCAGC AAACAAGCGC GACGACGACT CGAATTCCAA GTTCGTCAAG       660

TTGCCCTTTC ATAAGCTTTA CGGGGACTCG CTAGAAAATG TGGGAAGCGA CAAAAAACCG       720

GAAGTACGCC TATTGAAGAG GGCTGACGGT TATGAAGAAA TTATAATTAC CAACCAGCAA       780

AGTTTCTATT CGGTGGACTT GGAAGTGGGC ACGCCACCAC AGAACGTAAC GGTCCTGGTG       840

GACACAGGCT CCTCTGATCT ATGGATTATG GGCTCGGATA ATCCATACTG TTCTTCGAAC       900

AGTATGGGTA GTAGCCGGAG ACGTGTTATT GACAAACGTG ATGATTCGTC AAGCGGCGGA       960

TCTTTGATTA ATGATATAAA CCCATTTGGC TGGTTGACGG GAACGGGCAG TGCCATTGGC      1020

CCCACTGCTA CGGGCTTAGG AGGCGGTTCA GGTACGGCAA CTCAATCCGT GCCTGCTTCG      1080

GAAGCCACCA TGGACTGTCA ACAATACGGG ACATTTTCCA CTTCGGGCTC TTCTACATTT      1140

AGATCAAACA ACACCTATTT CAGTATTAGC TACGGTGATG GGACTTTTGC CTCCGGTACT      1200

TTTGGTACGG ATGTTTTGGA TTTAAGCGAC TTGAACGTTA CCGGGTTGTC TTTTGCCGTT      1260

GCCAATGAAA CGAATTCTAC TATGGGTGTG TTAGGTATTG GTTTGCCCGA ATTAGAAGTC      1320

ACTTATTCTG GCTCTACTGC GTCTCATAGT GGAAAAGCTT ATAAATACGA CAACTTCCCC      1380

ATTGTATTGA AAAATTCTGG TGCTATCAAA AGCAACACAT ATTCTTTGTA TTTGAACGAC      1440

TCGGACGCTA TGCATGGCAC CATTTTGTTC GGAGCCGTGG ACCACAGTAA ATATACCGGC      1500

ACCTTATACA CAATCCCCAT CGTAAACACT CTGAGTGCTA GTGGATTTAG CTCTCCCATT      1560
```

```
                                              -continued

CAATTTGATG TCACTATTAA TGGTATCGGT ATTAGTGATT CTGGGAGTAG TAACAAGACC      1620

TTGACTACCA CTAAAATACC TGCTTTGTCG GATTCCGGTA CTACTTTGAC TTATTTACCT      1680

CAAACAGTGG TAAGTATGAT CGCTACTGAA CTAGGTGCGC AATACTCTTC CAGGATAGGG      1740

TATTACGTAT TGGACTGTCC ATCTGATGAT AGTATGGAAA TAGTGTTCGA TTTTGGTGGT      1800

TTTCACATCA ATGCACCACT TTCGAGTTTT ATCTTGAGTA CTGGCACTAC ATGTCTTTTA      1860

GGTATTATCC CAACGAGTGA TGACACAGGT ACCATTTTGG GTGATTCATT TTTGACTAAC      1920

GCGTACGTGG TTTATGATTT GGAGAATCTT GAAATATCCA TGGCACAAGC TCGCTATAAT      1980

ACCACAAGCG AAAATATCGA AATTATCACA TCCTCTGTTC CAAGCGCCGT AAAGGCACCA      2040

GGCTATACAA ACACTTGGTC CACAAGTGCA TCTATTGTTA CCGGTGGTAA CATATTTACT      2100

GTAAATTCCT CACAAACTGC TTCCTTTAGC GGTAACCTGA CGACCAGTAC TGCATCCGCC      2160

ACTTCTACAT CAAGTAAAAG AAATGTTGGT GATCATATAG TTCCATCTTT ACCCCTCACA      2220

TTAATTTCTC TTCTTTTTGC ATTCATCTGA AAACCGTTGC ACAAAGTTTA GACATTCACA      2280

TCTCCAAGCC AGTTGGAGTT TCTGGCGGAA ATCGTTGCTC TCGCTTGGGC AAAGTTTTTT      2340

TTTATTATTA ATTTTTATT GTTACGTTGG CGGTCTTTAT TTTTACTTCA CAATAGTTTA       2400

TCTTACCCAC TAAGAATAGG TTACCATTTA TTCACATTTT TTTTTCTCAT TCCTAGTATA      2460

CTATTTACCT GGGATATGGC CTATAATCAA AGGCTTTAAT ATTCTAATAA TTCGTTTGGC     2520

ATCTAG                                                                2526

(2) INFORMATION FOR SEQ ID NO: 16:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (iii) HYPOTHETICAL: NO (iii) ANTI-SENSE: NO (v) FRAGMENT TYPE: internal (xi) SEQUENCE DESCRIPTION: SEQ ID NO: 16:

Phe Gln Asn Ala Leu Leu Val Arg Tyr Thr Lys Lys Val Pro Gln
1               5                   10                  15
```

YEAST STRAINS AND MODIFIED ALBUMINS

CROSS-REFERENCE TO RELATED APPLICATIONS

This application claims foreign priority benefits under 35 USC §119 to International Application Publication No. WO 95/23857, which was filed on Mar. 1, 1995 and which claims priority to GB 94042702, which was filed on Mar. 5, 1994.

FIELD OF THE INVENTION

The present invention relates to the production of recombinant human albumin (rHA) by yeast species.

BACKGROUND OF THE PRIOR ART

Human serum albumin (HSA) is a protein of 585 amino acids that is responsible for a significant proportion of the osmotic pressure of serum, and also functions as a carrier of endogenous and exogenous ligands. It is used clinically in the treatment of patients with severe burns, shock, or blood loss, and at present is produced commercially by extraction from human blood. The production of recombinant human albumin (rHA) in microorganisms has been disclosed in EP 330 451 and EP 361 991.

In recent years yeast species have been widely used as a host organisms for the production of heterologous proteins (reviewed by Romanos et al, 1992), including rHA (Sleep et al, 1990, 1991; Fleer et al, 1991). Yeasts are readily amenable to genetic manipulation, can be grown to high cell density on simple media, and as eukaryotes are suitable for production of secreted as well as cytosolic proteins.

When *S. cerevisiae* is utilised to produce rHA, the major secreted protein is mature 67 kDa albumin. However, a 45 kDa N-terminal fragment of rHA is also observed (Sleep et al, 1990). A similar fragment is obtained when rHA is expressed in Kluyveromyces sp. (Fleer et al, 1991) and *Pichia pastoris* (EP 510 693). The fragment has the same N-terminal amino acid sequence as mature rHA, but the carboxy terminus is heterogeneous and occurs between $Phe^{403}$ and $Val^{409}$ with the most common termini being $Leu^{407}$ and $Val^{409}$ Geisow et al, 1991), as shown below.

Sleep et al (1990) postulated that rHA fragment is produced within the cell and is not the result of extra-cellular proteolysis. These authors codon-optimised the HSA cDNA from $Glu^{382}$ to $Ser^{419}$ but this had no effect on production of rHA fragment. They noted that a potential Kex2p processing site in the rHA amino acid sequence, $Lys^{413}Lys^{414}$, is in close proximity to the heterogeneous carboxy terminus of the fragment, but neither use of a kex2 host strain (ie a strain harboring a mutation in the KEX2 gene such that it does not produce the Kex2p protease), nor removal of the potential cleavage site by site-directed mutagenesis of the codon for $Lys^{414}$, resulted in reduction in the amount of the fragment.

There is a vast array of yeast proteases which could, in principle, be degrading a desired protein product, including (in *S. cerevisiae*) yscA, yscB, yscY, yscS, other vacuolar proteinases, yscD, yscE, yscF (equivalent to kex2p), yscα, yscIV, yscG, yscH, yscJ, yscE and kex1.

Bourbonnais et al (1991) described an *S. cerevisiae* endoprotease activity specific for monobasic sites, an example of which ($Arg^{410}$) exists in this region of albumin. This activity was later found to be attributable to yeast aspartyl protease 3 (Yap3) (Bourbonnais et al, 1993), an enzyme which was originally described by Egel-Mitani et al (1990) as an endoprotease similar to Kex2p in specificity, in that it cleaved at paired basic residues. Further work suggested that Yap3p is able to cleave monobasic sites and between, and C-terminal to, pairs of basic residues, but that cleavage at both types of sites is dependent on the sequence context (Azaryan et al, 1993; Cawley et al, 1993).

As already discussed, the region of the C-terminus of rHA fragment contains both a monobasic ($Arg^{410}$) and a dibasic site ($Lys^{413}Lys^{414}$). However, even though a Kex2p-like proteolytic activity is present in human cells and is responsible for cleavage of the pro sequence of HSA C-terminal to a pair of arginine residues, the fragment discussed above is not known to be produced in humans. This indicates that the basic residues $Arg^{410}$, $Lys^{413}$ and $Lys^{414}$ are not recognised by this Kex2p-like protease, in turn suggesting that this region of the molecule may not be accessible to proteases in the secretory pathway. Thus, the Yap3p protease could not have been predicted to be responsible for the production of the 45 kDa fragment. In addition, Egel-Mitani et al (1990 Yeast 6, 127–137) had shown Yap3p to be similar to Kex2p

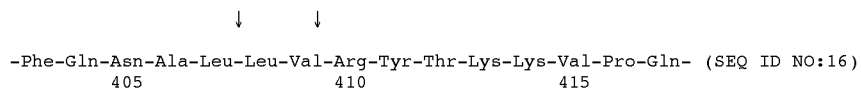

```
                   ↓         ↓
-Phe-Gln-Asn-Ala-Leu-Leu-Val-Arg-Tyr-Thr-Lys-Lys-Val-Pro-Gln- (SEQ ID NO:16)
      405                 410                 415
```

The amount of fragment produced, as a percentage of total rHA secreted, varies with both the strain and the secretion leader sequence utilised, but is never reduced to zero (Sleep et al, 1990). We have also found that the amount of fragment produced in high cell density fermentation (75–100 g/L cell dry weight) is approximately five times higher than in shake flask cultures.

The 45 kDa albumin fragment is not observed in serum-derived human serum albumin (HSA), and its presence as non-nature-identical material in the recombinant product is undesirable. The problem addressed by the present invention is to reduce the amount of the 45 kDa fragment in the product. The simplest and most obvious approach would have been to have purified it away from the full length albumin, as proposed by Gist-brocades in EP 524 681 (see especially page 4, lines 17–22). However, we have chosen a different approach, namely to try to avoid its production in the first place.

in cleaving the MFα propheromone. Since removal of the Kex2p function alone does not reduce the amount of the fragment produced, there was no reason to suppose that removal of the Yap3p function would be beneficial. Indeed, Bourbonnais et al (1993) showed that yap3 strains had a decreased ability to process prosomatostatin, and therefore taught away from using yap3 strains in the production of heterologous proteins.

SUMMARY OF THE INVENTION

The solution to the problem identified above is, in accordance with the invention, to avoid or at least reduce production of the fragment in the initial fermentation, rather than to remove it during purification of the albumin. We have now found that, out of the 20 or more yeast proteases which are so far known to exist, it is in fact the Yap3p protease which is largely responsible for the 45 kD fragment of rHA produced in yeast. The present invention provides a method for substantially reducing the amount of a 45 kDa fragment produced when rHA is secreted from yeast species. The reduction in the amount of fragment both improves recovery of rHA during the purification process, and provides a higher quality of final product. A further, and completely unexpected, benefit of using yap3 strains of yeast is that they can produce 30–50% more rHA than strains having the Yap3p function. This benefit cannot be accounted for merely by the reduction of rHA fragment from~15% to 3–5%.

Thus, one aspect of the present invention provides a process for preparing albumin by secretion from a yeast genetically modified to produce and secrete the albumin, comprising culturing the yeast in a culture medium such that albumin is secreted into the medium, characterised in that the yeast cells have a reduced level of yeast aspartyl protease 3 proteolytic activity.

Preferably, the said proteolytic activity is an endoprotease activity specific for monobasic sites and for paired basic amino acids in a polypeptide.

Suitably, the yeast is *S. cerevisiae* which lacks a functional YAP3 gene. However, the invention is not limited to the use of *S. cerevisiae*, since the problem of 45 kDa fragment production is found also in other yeast genera, for example Pichia and Kluyveromyces, which shows that they have equivalent proteases (ie Yap3p proteolytic activity); see Clerc et al (1994), page 253. We have confirmed this by hybridisation analysis to locate homologues of Yap3p in non-Saccharomyces genera. A gene is regarded as a homologue, in general, if the sequence of the translation product has greater than 50% sequence identity to Yap3p. In non-Saccharomyces genera, the Yap3p-like protease and its gene may be named differently, but this does not of course alter their essential nature.

The level of fragment can be reduced still further if, as well as substantially eliminating the Yap3p proteolytic activity, the Kex2p function is also substantially eliminated even though, as mentioned above, elimination of the Kex2p function alone does not affect the level of fragment. As in the case of Yap3p, the Kex2p function is not restricted to Saccharomyces; see Gellissen et al (1992), especially the sentence bridging pages 415 and 416, showing that Pichia has a Kex2p function. The genes encoding the Kex2p equivalent activity in *Kluyveromyces lactis* and *Yarrowia lipolytica* have been cloned (Tanguy-Rougeau et al, 1988; Enderlin & Ogrydziak, 1994).

A suitable means of eliminating the activity of a protease is to disrupt the host gene encoding the protease, thereby generating a non-reverting strain missing all or part of the gene for the protease (Rothstein, 1983). Alternatively, the activity can be reduced or eliminated by classical mutagenesis procedures or by the introduction of specific point mutations by the process of transplacement (Winston et al, 1983). Preferably, the activity of the enzyme is reduced to at most 50% of the wild-type level, more preferably no more than 25%, 10% or 5%, and most preferably is undetectable. The level of Yap3p proteolytic activity may be measured by determining the production of the 45 kDa fragment, or by the $^{125}I$-$\beta_h$-lipoprotein assay-of Azaryan et al (1993), also used by Cawley et al (1993). Kex2p proteolytic activity may similarly be measured by known assays, for example as set out in Fuller et al (1989).

The albumin may be a human albumin, or a variant thereof, or albumin from any other animal.

By "variants" we include insertions, deletions and substitutions, either conservative or non-conservative, where such changes do not substantially alter the oncotic, useful ligand-binding or non-immunogenic properties of albumin. In particular, we include naturally-occurring polymorphic variants of human albumin; fragments of human albumin which include the region cleaved by Yap3p, for example those fragments disclosed in EP 322 094 (namely HSA (1–n), where n is 369 to 419) which are sufficiently long to include the Yap3p-cleaved region (ie where n is 403 to 419); and fusions of albumin (or Yap3p-cleavable portions thereof) with other proteins, for example the kind disclosed in WO 90/13653.

By "conservative substitutions" is intended swaps within groups such as Gly, Ala; Val, Ile, Leu; Asp, Glu; Asn, Gln; Ser, Thr; Lys, Arg; and Phe, Tyr.

Such variants may be made using the methods of protein engineering and site-directed mutagenesis as described below.

A second aspect of the invention provides a modified albumin having at least 90% sequence identity to a naturally-occurring albumin, which naturally-occurring albumin is susceptible to cleavage with the *S. cerevisiae* yeast aspartyl protease 3 (Yap3p) when expressed in yeast, characterised in that the modified albumin is not susceptible to such cleavage.

Preferably, the modified albumin lacks a monobasic amino acid present in the naturally-occurring albumin protein. Suitably, the said monobasic amino acid is arginine. Conveniently, the modified albumin additionally lacks a pair of basic amino acids present in the naturally-occurring albumin, especially any of Lys, Lys; Lys, Arg; Arg, Lys; or Arg, Arg. Thus, in one particular embodiment, the naturally-occurring albumin is human albumin and the modified protein lacks $Arg^{410}$ and, optionally, one or both $Lys^{413}Lys^{414}$ lysines. For example, the modified albumin may be human albumin having the amino acid changes R410A, K413Q, K414Q. Equivalent modifications in bovine serum albumin include replacing the $Arg^{408}$ and/or one or both of $Arg^{411}Lys^{412}$. The person skilled in the art will be able to identify monobasic sites and pairs of basic residues in other albumins without difficulty.

The numbering of the residues corresponds to the sequence of normal mature human albumin. If the albumin is a variant (for example a polymorphic form) having a net deletion or addition of residues N-terminal to the position identified, then the numbering refers to the residues of the variant albumin which are aligned with the numbered positions of normal albumin when the two sequences are so aligned as to maximise the apparent homology.

A third aspect of the invention provides a polynucleotide encoding such a modified albumin.

The DNA is expressed in a suitable yeast (either the DNA being for a modified albumin, or the yeast lacking the Yap3p function) to produce an albumin. Thus, the DNA encoding the albumin may be used in accordance with known techniques, appropriately modified in view of the teachings contained herein, to construct an expression vector, which is then used to transform an appropriate yeast cell for the expression and production of the albumin.

The DNA encoding the albumin may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. The vector is then introduced into the host through standard techniques and, generally, it will be necessary to select for transformed host cells.

Host cells that have been transformed by the recombinant DNA of the invention are then cultured for a sufficient time and under appropriate conditions known to those skilled in the art in view of the teachings disclosed herein to permit the expression and secretion of the albumin, which can then be recovered, as is known.

Useful yeast plasmid vectors are pRS403–406 and pRS413–416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413–416 are Yeast Centromere plasmids (YCps). Other yeast expression plasmids are disclosed in EP-A-258 067, EP-A-286 424 and EP-A-424 117.

The polynucleotide coding sequences encoding the modified albumin of the invention may have additional differences to those required to produce the modified albumin. For example, different codons can be substituted which code for the same amino acid(s) as the original codons. Alternatively, the substitute codons may code for a different amino acid that will not affect the activity or immunogenicity of the albumin or which may improve its activity or immunogenicity, as well as reducing its susceptibility to a Yap3p protease activity. For example, site-directed mutagenesis or other techniques can be employed to create single or multiple mutations, such as replacements, insertions, deletions, and transpositions, as described in Botstein and Shortle (1985). Since such modified coding sequences can be obtained by the application of known techniques to the teachings contained herein, such modified coding sequences are within the scope of the claimed invention.

Exemplary genera of yeast contemplated to be useful in the practice of the present invention are Pichia, Saccharomyces, Kluyveromyces, Candida, Torulopsis, Hansenula (now reclassified as Pichia), Histoplasma, Schizosaccharomyces, Citeromyces, Pachysolen, Debaromyces, Metschunikowia, Rhodosporidium, Leucosporidium, Botryoascus, Sporidiobolus, Endomycopsis, and the like. Preferred genera are those selected from the group consisting of Pichia, Saccharomyces, Kluyveromyces, Yarrowia and Hansenula. Examples of Saccharomyces sp. are S. cerevisiae, S. italicus and S. rouxii. Examples of Kluyveromyces sp. are K. fragilis and K. lactis. Examples of Hansenula (Pichia) sp. are H. polymorpha (now Pichia angusta), H. anomala (now P. anomala) and P. pastoris. Y. lipolytica is an example of a suitable Yarrowia species.

Methods for the transformation of S. cerevisiae are taught generally in EP 251 744, EP 258 067 and WO 90/01063, all of which are incorporated herein by reference. Suitable promoters for S. cerevisiae include those associated with the PGK1 gene, GAL1 or GAL10 genes, CYC1, PHO5, TRP1, ADH1, ADH2, the genes for glyceraldehyde-3-phosphate dehydrogenase, hexokinase, pyruvate decarboxylase, phosphofructokinase, triose phosphate isomerase, phosphoglucose isomerase, glucokinase, α-mating factor pheromone, a-mating factor pheromone, the PRB1 promoter, the GPD1 promoter, and hybrid promoters involving hybrids of parts of 5' regulatory regions with parts of 5' regulatory regions of other promoters or with upstream activation sites (eg the promoter of EP-A-258 067).

Convenient regulatable promoters for use in *Schizosaccharomyces pombe* are the thiamine-repressible promoter from the nmt gene as described by Maundrell (1990) and the glucose-repressible fbp1 gene promoter as described by Hoffman & Winston (1990).

Methods of transforming Pichia for expression of foreign genes are taught in, for example, Cregg et al (1993), and various Phillips patents (eg U.S. Pat. No. 4,857,467, incorporated herein by reference), and Pichia expression kits are commercially available from Invitrogen BV, Leek, Netherlands, and Invitrogen Corp., San Diego, Calif. Suitable promoters include AOX1 and AOX2.

The Gellissen et al (1992) paper mentioned above and Gleeson et al (1986) *J. Gen. Microbiol.* 132, 3459–3465 include information on Hansenula vectors and transformation, suitable promoters being MOX1 and FMD1; whilst EP 361 991, Fleer et al (1991) and other publications from Rhone-Poulenc Rorer teach how to express foreign proteins in Kluyveromyces spp., a suitable promoter being PGK1.

The transcription termination signal is preferably the 3' flanking sequence of a eukaryotic gene which contains proper signals for transcription termination and polyadenylation. Suitable 3' flanking sequences may, for example, be those of the gene naturally linked to the expression control sequence used, ie may correspond to the promoter. Alternatively, they may be different in which case the termination signal of the S. cerevisiae ADH1 gene is preferred.

The albumin is initially expressed with a secretion leader sequence, which may be any leader effective in the yeast chosen. Leaders useful in *S. cerevisiae* include that from the mating factor α polypeptide (MFα–1) and the hybrid leaders of EP-A-387 319. Such leaders (or signals) are cleaved by the yeast before the mature albumin is released into the surrounding medium. When the yeast strain lacks Kex2p activity (or equivalent) as well as being yap3, it may be advantageous to choose a secretion leader which need not be cleaved from the albumin by Kex2p. Such leaders include those of *S. cerevisiae* invertase (SUC2) disclosed in JP 62-096086 (granted as 91/036516), acid phosphatase (PHO5), the pre-sequence of MFα–1, β-glucanase (BGL2) and killer toxin; *S. diastaticus* glucoamylase II; *S. carlsbergensis* α-galactosidase (MEL1); *K. lactis* killer toxin; and Candida glucoamylase.

Various non-limiting embodiments of the invention will now be described by way of example and with reference to the accompanying drawings in which.

Figure 4:
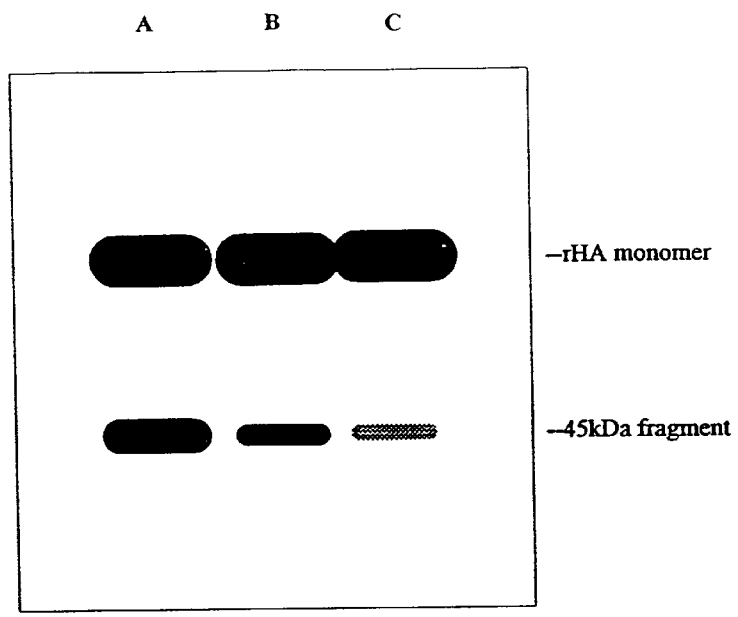
FIG. 4 is a comparison of rHA fragment production by wild-type and protease-disrupted strains, presented as a drawing of an anti-HSA Western blot of culture supernatant from shake flask cultures separated by non-reducing 10% xSDS/PAGE, in which Track A corresponds to DB1 cir° pAYE316, Track B corresponds to DXY10 cir° pAYE316 (yap3 strain), and Track C corresponds to ABB50 cir° pAYE316 (yap3, kex2 strain)
Figure 5:
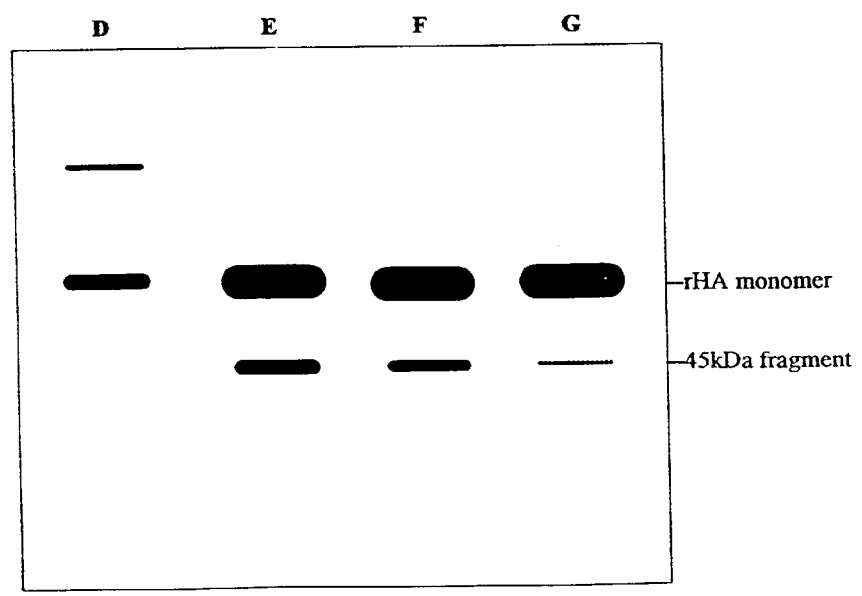
Figure 6:
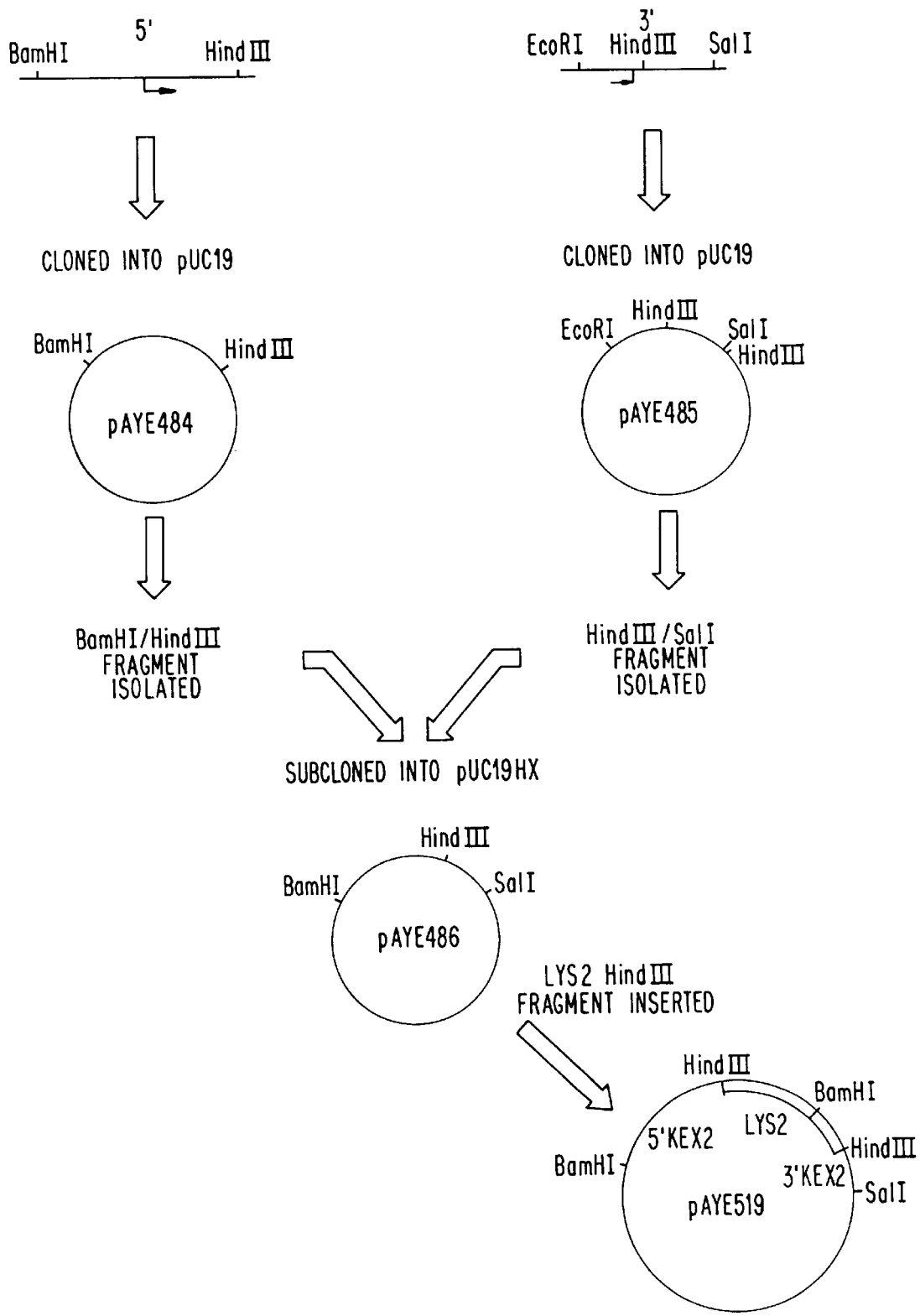

FIG. 5 is similar to FIG. 4 but shows Coomassie Brilliant Blue stained 12.5% SDS Phastgel (Pharmacia) of culture supernatants from fed batch fermentations, namely Track D for the HSA standard, Track E for DB1 cir° pAYE316, Track F for DB1 Δkex2 cir° pAYE522, and Track G for DXY10 cir° pAYE522; and FIG. 6 is a scheme for the construction of pAYE519.

DETAILED DESCRIPTION OF THE INVENTION

All standard recombinant DNA procedures are as described in Sambrook et al (1989) unless otherwise stated. The DNA sequences encoding HSA are derived from the cDNA disclosed in EP 201 239.

EXAMPLE 1

Modification of the HSA cDNA

In order to investigate the role of endoproteases in the generation of rHA fragment, the HSA cDNA (SEQ ID NO:1) (which includes a sequence encoding the artificial secretion leader sequence of WO 90/01063)) was modified by site-directed mutagenesis. Three separate changes were made to the HSA sequence (SEQ ID NO: 2). The first, using the mutagenic primer FOG1, changed the $Arg^{410}$ codon only, replacing it with an Ala codon, leaving intact the dibasic site, $Lys^{413}Lys^{414}$. The second change, using primer FOG2, changed the residues 407–409, including the C-terminal residues of fragment, from LeuLeuVal to AlaValAla. The third change, using the primer FOG3, altered residues 410–414 from ArgTyrThrLysLys (SEQ ID NO: 3) to AlaTyrThrGlnGln (SEQ ID NO: 4). The oligonucleotides encoded not only the amino acid changes, but also conservative base changes that create either a PvuII or an SpeI restriction site in the mutants to facilitate detection of the changed sequences.

Figure 1:
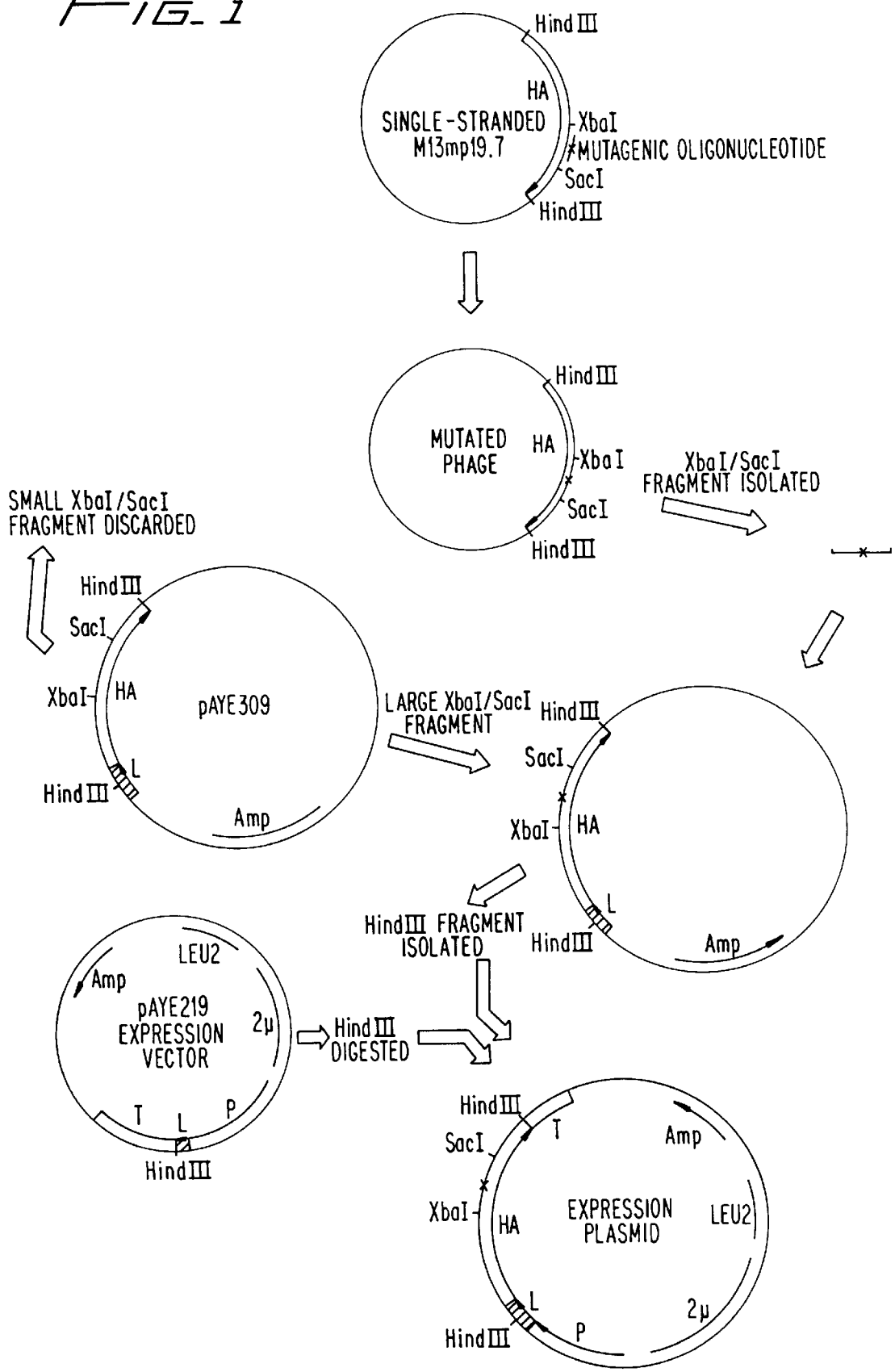
FIG. 1 is a general scheme for the construction of mutated rHA expression plasmids, in which HA is a human albumin coding sequence, L is a sequence encoding a secretion leader, P is the PRB1 promoter, T is the ADH1 terminator, amp is an ampicillin resistance gene and LEU2 is the leucine selectable marker.
Figure 2:
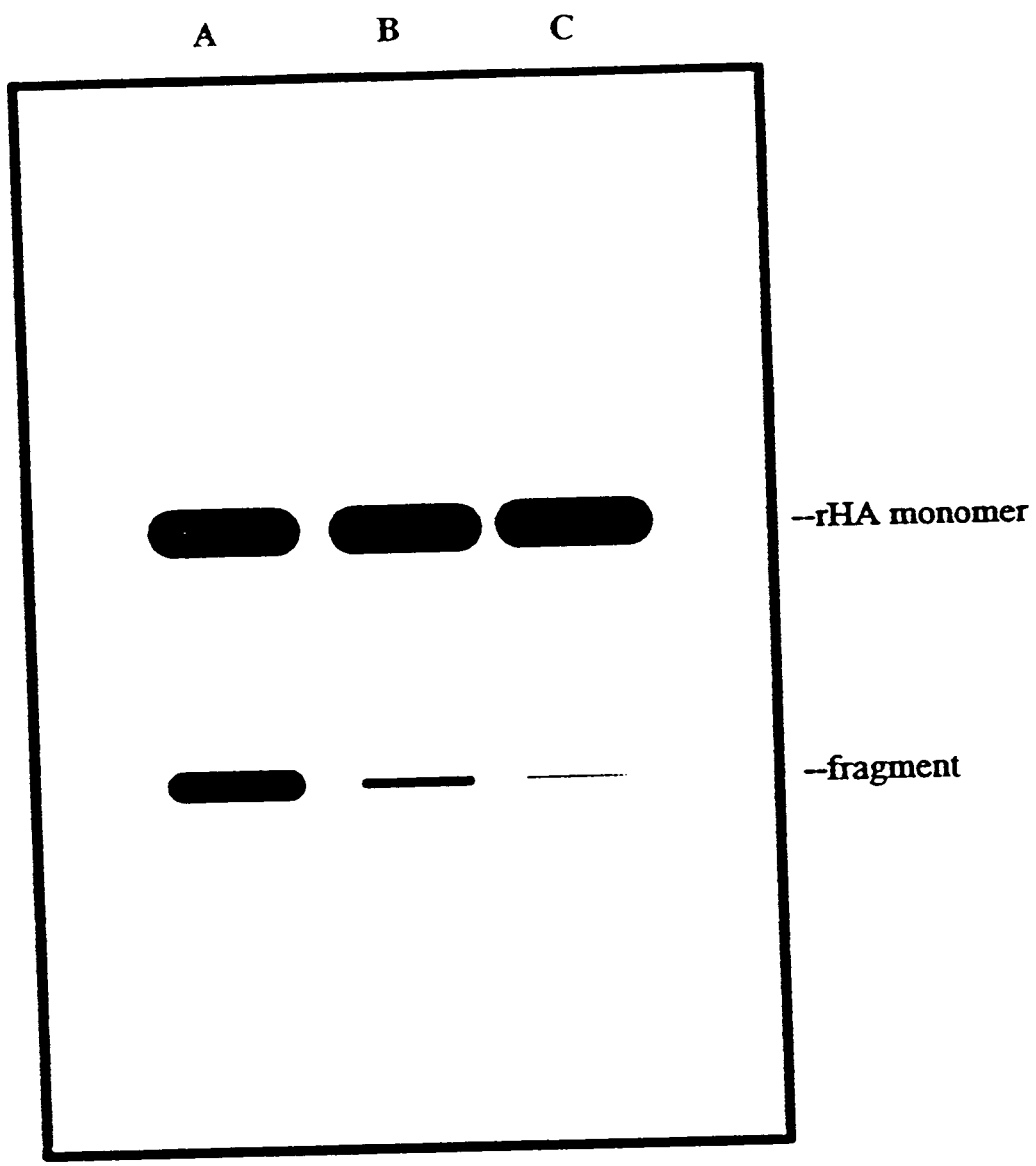
FIG. 2 is a drawing representing a Western blot analysis of mutant rHA secreted by S. cerevisiae, in which Track A represents the culture supernatant from DB1 cir° pAYE316 (normal rHA), Track B represents the culture supernatant from DB1 cir⁺ pAYE464 (alteration 1), and Track C represents the culture supernatant from DB1 cir⁺ pAYE468 (alteration 3)

Single-stranded DNA of an M13mp19 clone, mp19.7 (EP 201 239; FIG. 2), containing the HSA cDNA was used as the template for the mutagenesis reactions using the In Vitro Mutagenesis System, Version 2 (Amersham International plc) according to the manufacturer's instructions. Individual plaques were selected and sequenced to confirm the presence of the mutations. Double stranded RF DNA was then made from clones with the expected changes and the DNA bearing the mutation was excised on an XbaI/SacI fragment (FIG. 1). This was used to replace the corresponding wild-type fragment of pAYE309 (EP 431 880; FIG. 2). The presence of the mutated XbaI/SacI fragment within the plasmid was checked by digesting with PvuII or SpeI as appropriate. These HindIII fragments were excised and inserted into the expression vector pAYE219 (FIG. 1) to generate the plasmids pAYE464 (alteration 1, R410A), pAYE470 (alteration 2, L407A, L408V, V409A) and pAYE468 (alteration 3, R410A, K413Q, K414Q). These expression plasmids comprise the S. cerevisiae PRB1 promoter (WO 91/02057) driving expression of the HSA/MFα1 leader sequence (WO 90/01063) fused in-frame with the mutated HA coding sequence which is followed by the ADH1 transcription terminator. The plasmids also contain part of the 2 μm plasmid to provide replication functions and the LEU2 gene for selection of transformants.

pAYE464, pAYE470 and pAYE468 were introduced into S. cerevisiae DB1 cir⁺ (a, leu2; Sleep et al, 1990) by transformation and individual transformants were grown for 3 days at 30° C. in 10 ml YEPS (1% w/v yeast extract, 2% w/v peptone, 2% w/v sucrose) and then the supernatants were examined by anti-HSA Western blot for the presence of the rHA fragment. The Western blots clearly showed that fragment was still produced by the strains harboring pAYE464, although the level was reduced slightly compared to the control expressing wild-type rHA. The mutations in the plasmid pAYE470 appeared to have no effect on the generation of fragment. However, DB1 cir⁺ pAYE468 showed a novel pattern of HSA-related bands, with little or no fragment.

One example of each of DB1 cir⁺ pAYE464 and DB1 cir⁺ pAYE468 were grown to high cell density by fed batch culture in minimal medium in a fermenter (Collins, 1990). Briefly, a fermenter of 10 L working volume was filled to 5 L with an initial batch medium containing 50 mL/L of a concentrated salts mixture (Table 1), 10 mL/L of a trace elements solution (Table 2), 50 mL/L of a vitamins mixture (Table 3) and 20 g/L sucrose. An equal volume of feed medium containing 100 mL/L of the salts mixture, 20 mL/L of the trace elements mixture, 100 mL/L of vitamins solution and 500 g/L sucrose was held in a separate reservoir connected to the fermenter by a metering pump. The pH was maintained at 5.7±0.2 by the automatic addition of ammonium hydroxide or sulphuric acid, and the temperature was maintained at 30° C. The stirrer speed was adjusted to give a dissolved oxygen tension of >20% air saturation at 1 v/v/min air flow rate.

TABLE 1

Salts Mixture

| Chemical | Concentration (g/L) |
|---|---|
| $KH_2PO_4$ | 114.0 |
| $MgSO_4$ | 12.0 |
| $CaCl_2.6H_2O$ | 3.0 |
| $Na_2EDTA$ | 2.0 |

TABLE 2

Trace Elements Solution

| Chemical | Concentration (g/L) |
|---|---|
| $ZnSO_4.7H_2O$ | 3.0 |
| $FeSO_4.7H_2O$ | 10.0 |
| $MnSO_4.4H_2O$ | 3.2 |
| $CuSO_4.5H_2O$ | 0.079 |
| $H_3BO_3$ | 1.5 |
| KI | 0.2 |
| $Na_2MoO_4.2H_2O$ | 0.5 |
| $CoCl_2.6H_2O$ | 0.56 |
| $H_3PO_4$ | 75 mL/L |

TABLE 3

Vitamins Solution

| Chemical | Concentration (g/L) |
|---|---|
| Ca pantothenate | 1.6 |
| Nicotinic acid | 1.2 |
| m inositol | 12.8 |
| Thiamine HCl | 0.32 |
| Pyridoxine HCl | 0.8 |
| Biotin | 0.008 |

The fermenter was inoculated with 100 mL of an overnight culture of S. cerevisiae grown in buffered minimal medium (Yeast nitrogen base [without amino acids, without ammonium sulphate, Difco] 1.7 g/L, $(NH_4)_2SO_4$ 5 g/L, citric acid monohydrate 6.09 g/L, $Na_2HPO_4$ 20.16 g/L, sucrose 20 g/L, pH6.5). The initial batch fermentation proceeded until the carbon source had been consumed, at which point the metering pump was switched on and the addition of feed was computer controlled (the micro MFCS system, B. Braun, Melsungen, Germany) using an algorithm based on that developed by Wang et al (1979). A mass spectrometer was used in conjunction with the computer control system to monitor the off gases from the fermentation and to control the addition of feed to maintain a set growth rate (eg 0.1 $h^{-1}$). Maximum conversion of carbon substrate into biomass is achieved by maintaining the respiratory coefficient below 1.2 (Collins, 1990) and, by this means, cell densities of approximately 100 g/L cell dry weight can be achieved. The culture supernatants were compared with those of a wild-type rHA producer by Coomassie-stained SDS/PAGE and by Western blot. These indicated (FIG. 2) that, whilst elimination of the monobasic $Arg^{410}$ (pAYE464) did reduce the level of the fragment by a useful amount, removal of both potential protease sites (pAYE468) almost abolished the 45 kDa fragment.

The above data suggested that the generation of rHA fragment might be due to endoproteolytic attack, though the absence of an effect of removal of the potential Kex2p site $Lys^{413}Lys^{414}$ (Sleep et al, 1990, and confirmed by other studies not noted here) unless combined with elimination of $Arg^{410}$, had suggested a complex etiology. The reduction in the amount of fragment with the mutated rHA could in principle be due to an effect of the changes on the kinetics of folding of the molecule and not due to the removal of protease cleavage sites.

EXAMPLE 2

Disruption of the YAP3 Gene

The YAP3 gene encoding yeast aspartyl protease 3 was mutated by the process of gene disruption (Rothstein 1983) which effectively deleted part of the YAP3 coding sequence, thereby preventing the production of active Yap3p.

Four oligonucleotides suitable for PCR amplification of the 5' and 3' ends of the YAP3 gene (Egel-Mitani et al, 1990) were synthesised using an Applied Biosystems 380B Oligonucleotide Synthesiser. To assist the reader, we include as SEQ15 the sequence of the YAP3 gene, of which 541–2250 is the coding sequence.

```
5' end
YAP3A:    5'-CGTCAGACCTTGCATGCAGCCAAGACACCCTCACATAGC-3'      (SEQ ID NO:5)

YAP3B:    5'-CCGTTACGTTCTGTGGTGGCATGCCCACTTCCAAGTCCACCG-3'   (SEQ ID NO:6)

3' end
YAP3C:    5'-GCGTCTCATAGTGGAAAAGCTTCTAAATACGACAACTTCCCC-3'   (SEQ ID NO:7)

YAP3D:    5'-CCCAAAATGGTACCTGTGTCATCACTCGTTGGGATAATACC-3'    (SEQ ID NO:8)
```

Figure 3:
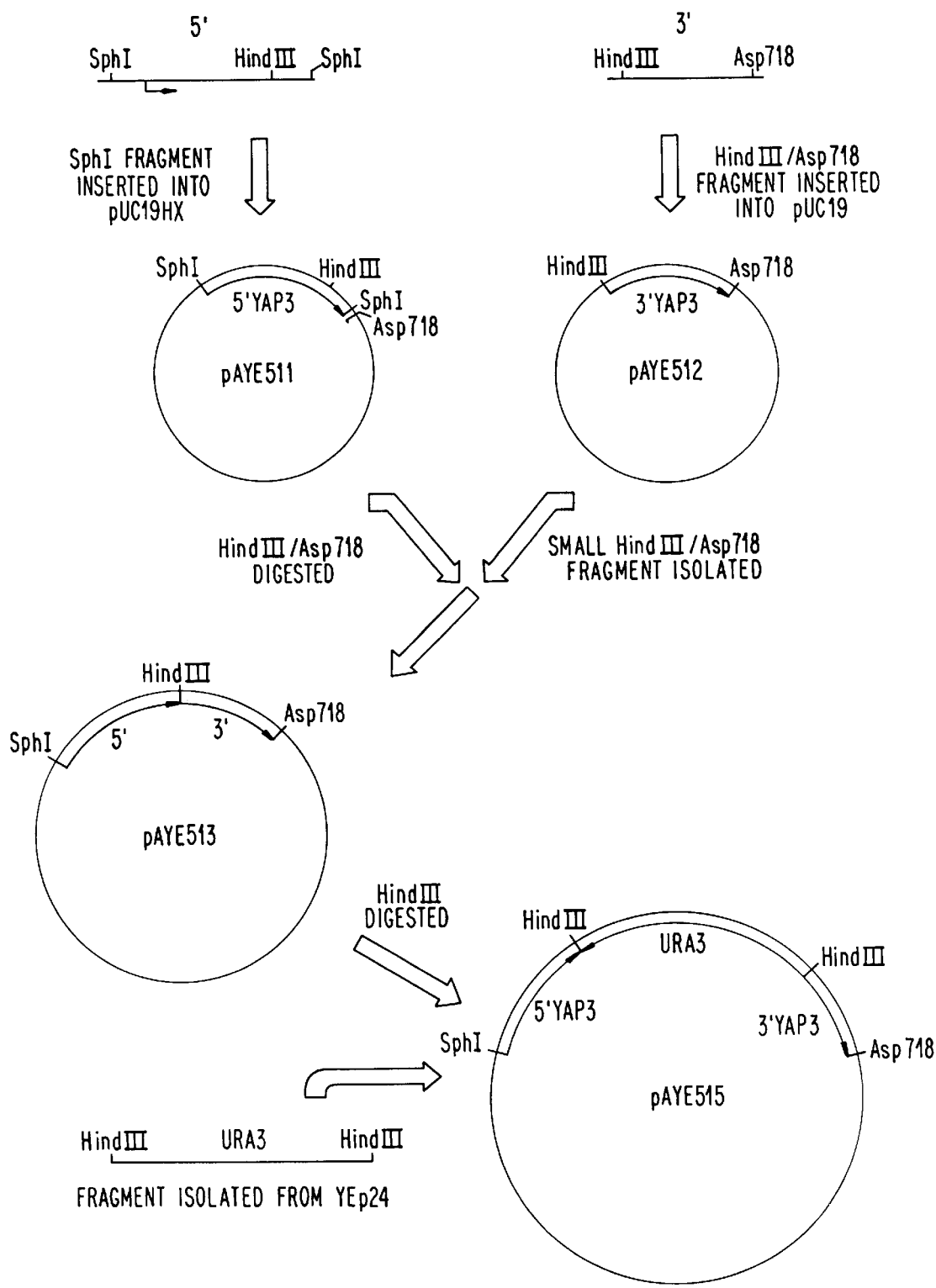
FIG. 3 is a scheme of the construction of pAYE515.

PCR reactions were carried out to amplify individually the 5' and 3' ends of the YAP3 gene from S. cerevisiae genomic DNA (Clontech Laboratories, Inc). Conditions were as follows: 2.5 μg/ml genomic DNA, 5 μg/ml of each primer, denature at 94° C. 61 seconds, anneal at 37° C. 121 secs, extend at 72° C. 181 secs for 40 cycles, followed by a 4° C. soak, using a Perkin-Elmer-Cetus Thermal Cycler and a Perkin-Elmer-Cetus PCR kit according to the manufacturer's recommendations. Products were analysed by gel electrophoresis and were found to be of the expected size. The 5' fragment was digested with SphI and cloned into the SphI site of pUC19HX (pUC19 lacking a HinduIII site) to give pAYE511 (FIG. 3), in which the orientation is such that YAP3 would be transcribed towards the KpnI site of the pUC19HX polylinker. The 3' YAP3 fragment was digested with HindIII and Asp718 (an isoschizomer of KpnI) and ligated into pUC19 digested with HindIII/Asp718 to give pAYE512. Plasmid DNA sequencing was carried out on the inserts to confirm that the desired sequences had been cloned. The HindIII/Asp718 fragment of pAYE512 was then subcloned into the corresponding sites of pAYE511 to give pAYE513 (FIG. 3), in which the 5' and 3' regions of YAP3 are correctly orientated with a unique HinduIII site between them. The URA3 gene was isolated from YEp24 (Botstein et al, 1979) as a HindIII fragment and then inserted into this site to give pAYE515 (FIG. 3), with URA3 flanked by the 5' and 3' regions of YAP3, and transcribed in the opposite direction to YAP3.

A ura3 derivative of strain DB1 cir° pAYE316 (Sleep et al, 1991) was obtained by random chemical mutagenesis and selection for resistance to 5-fluoro-orotic acid (Boeke et al, 1987). The strain was grown overnight in 100 mL buffered minimal medium and the cells were collected by centrifugation and then washed once with sterile water. The cells were then resuspended in 10 mL sterile water and 2 mL aliquots were placed in separate 15 mL Falcon tubes. A 5 mg/mL solution of N-methyl-'-nitro-N-nitrosoguanidine (NTG) was then added to the tubes as follows: 0 μL, 20 μL, 40 μL, 80 μL or 160 μL. The cells were then incubated at 30° C. for 30 min and then centrifuged and washed three times with sterile water. Finally, the cells were resuspended in 1 mL YEP (1% w/v yeast extract, 2% w/v Bacto peptone) and stored at 4° C. The percentage of cells that survived the mutagenic treatment was determined by spreading dilutions of the samples on YEP plates containing 2% w/v sucrose and incubating at 30° C. for 3 days. Cells from the treatment which gave approximately 50% survival were grown on YEP plates containing 2% w/v sucrose and then replica-plated onto YNB minimal medium containing 2% w/v sucrose and supplemented with 5-fluoro-orotic acid (1 mg/mL) and uracil (50 μg/mL). Colonies able to grow on this medium were purified, tested to verify that they were unable to grow in the absence of uracil supplementation and that this defect could be corrected by introduction of the URA3 gene by transformation. One such strain, DBU3 cir° pAYE316, was transformed with the SphI/Asp718 YAP3-URA3-YAP3 fragment of pAYE515 with selection for Ura$^+$ colonies. A Southern blot of digested genomic DNA of a number of transformants was probed with the 5' and 3' ends of the YAP3 gene and confirmed the disruption of the YAP3 gene. An anti-HSA Western blot of YEPS shake-flask supernatants of two transformants indicated that disruption of YAP3 markedly reduced rHA fragment levels.

One yap3 derivative of DBU3 cir° pAYE316, designated DXY10 cir° pAYE316, was grown several times by fed-batch fermentation in minimal medium to high cell dry weight. When supernatants were examined by Coomassie-stained PAGE and anti-HSA Western blot (FIGS. 4 and 5), the reduction in the level of rHA 45 kDa fragment was clearly apparent; estimates of the amount of the degradation product vary from ⅓ to ⅕ of the levels seen with the YAP3 parent. The amount of rHA produced was not adversely affected by the yap3 mutation, indeed DXY10 cir° pAYE316 was found to produce 30–50% more rHA than the YAP3 equivalent, DB1 cir° pAYE316. Despite the fact that cleavage of the leader sequence from the HA sequence is C-terminal to a pair of basic residues, the rHA was found to have the correct N-terminus.

The fermentation broth was centrifuged to remove the cells and then subject to affinity chromatographic purification as follows. The culture supernatant was passed through a Cibacron Blue F3GA Sepharose column (Pharmacia) which was then washed with 0.1M phosphate glycine buffer, pH8.0. The rHA was then eluted from the column with 2M NaCl, 0.1M phosphate glycine, pH8.0, at which point it was >95 % pure. It may be purified further by techniques known in the art.

The albumin may alternatively be purified from the culture medium by any of the variety of known techniques for purifying albumin from serum or fermentation culture medium, for example those disclosed in WO 92/04367, Maurel et al (1989), Curling (1980) and EP 524 681.

EXAMPLE 3

Disruption of the KEX2 Gene in a yap3 Strain

To construct a strain lacking both Yap3p and Kex2p activity, a lys2 derivative of yeast strain DXY10 cir° (pAYE316) was obtained by random chemical mutagenesis and selection for resistance to α-amino adipate (Barnes and Thorner, 1985). Cells were mutagenised as in Example 2 and then plated on YNB minimal medium containing 2% w/v sucrose and supplemented with 2 mg/mL DL-α-amino adipate as the sole nitrogen source and 30 µg/mL lysine. Colonies able to grow on this medium were purified and tested to verify that they were unable to grow in the absence of lysine supplementation and that this defect could be corrected by the introduction of the LYS2 gene by transformation. This strain was then mutated by the process of gene disruption which effectively disrupted part of the KEX2 coding sequence, thereby preventing production of active Kex2p. To assist the reader, the sequence of the KEX2 gene is reproduced herein as SEQ14, of which 1329–3773 is the coding sequence.

Four oligonucleotides suitable for PCR amplification of the 5' and 3' ends of the KEX2 gene (Fuller et al, 1989) were synthesised using an Applied Biosystems 380B Oligonucleotide Synthesiser.

soak, using a Perkin-Elmer-Cetus Thermal Cycler and a Perkin-Elmer-Cetus PCR kit according to the manufacturer's recommendations. Products were analysed by gel electrophoresis and were found to be of the expected size (0.9 kb for the 5' product and 0.62 kb for the 3' product). The 5' product was digested with BamHI and HindIII and the 3' product was digested with HindIII and SalI and then the two fragments were together cloned into pUC19HX digested with BamHI and SalI. A 4.8 kb HindIII fragment comprising the S. cerevisiae LYS2 gene (Barnes & Thorner, 1985) was then inserted into the resulting plasmid at HindIII (ie between the two KEX2 fragments) to form pAYE519 (FIG. 6).

The lys2 derivative of DXY10 cir° (pAYE316), lys2–16, was transformed with the 6.0 kb KEX2-LYS2-KEX2 fragment of pAYE519, selecting for Lys$^{30}$ colonies. A Southern blot of digested genomic DNA of a number of transformants was probed with the 5' and 3' ends of the KEX2 gene and confirmed the disruption of the KEX2 gene. An anti-HSA Western blot of YEPS shake-flask culture supernatants of these transformants indicated that disruption of KEX2 in a yap3 strain reduced the level of rHA fragment still further, despite the lack of an effect of disruption of KEX2 alone in Example 4 below. Analysis of the rHA produced by one such strain, ABB50, indicated that the leader sequence was incorrectly processed, leading to an abnormal N-terminus.

The strain ABB50 (pAYE316) was cured of its plasmid (Sleep et al, 1991) and transformed with a similar plasmid, pAYE522, in which the hybrid leader sequence was replaced by the S. cerevisiae invertase (SUC2) leader sequence such that the encoded leader and the junction with the HSA sequence were as follows:

```
MLLQAFLFLLAGFAAKISA↓DAHKS    (SEQ ID NO:13)
   Invertase leader HSA
```

In this construct, cleavage of the leader sequence from HSA does not rely upon activity of the Kex2 protease. The strain ABB50 (pAYE522) was found to produce rHA with a similarly very low level of rHA fragment, but in this instance the N-terminus corresponded to that of serum-derived HSA, ie there was efficient and precise removal of the leader sequence.

EXAMPLE 4

Disruption of the KEX2 Gene alone (Comparative Example)

By a similar method to that disclosed in Example 3 the KEX2 gene was disrupted in S. cerevisiae. This strain had

```
5' end
KEX2A:   5'-CCATCTGGATCCAATGGTGCTTTGGCCAAATAAATAGTTTCAGC-3'    (SEQ ID NO:9)

KEX2B:   5'GCTTCTTTTACCGGTAACAAGCTTGAGTCCATTGG-3'              (SEQ ID NO:10)

3' end
KEX2C:   5'-GGTAAGGTTTAGTCGACCTATTTTTTGTTTTGTCTGC-3'           (SEQ ID NO:11)

KEX2D:   5'-GGAAACGTATGAATTCGATATCATTGATACAGACTCTGAGTACG-3'    (SEQ ID NO:12)
```

PCR reactions were carried out to amplify individually the 5' and 3' ends of the KEX2 gene from S. cerevisiae genomic DNA (Clontech Laboratories Inc).

Conditions were as follows: 2.5 µg/ml genomic DNA, 5 µg/ml of each primer, denature 94° C. 61s, anneal 37° C. 121s, extend 72° C. 181s for 40 cycles, followed by a 4° C.

the Yap3p proteolytic activity and was therefore not within the scope of the invention. When this strain was grown in fed batch fermentation the rHA produced contained similar amounts of fragment to that produced by strains with an intact KEX2 gene. In addition, the overall level of rHA was reduced and the leader sequence was not correctly processed, leading to an abnormal N-terminus.

EXAMPLE 5

Identification of Equivalent Protease in Pichia

As noted above, non-Saccharomyces yeast similarly produce the undesirable fragment of rHA and therefore have the Yap3p proteolytic activity. We have confirmed this by performing Southern hybridisations of *Pichia angusta* DNA, using the *S. cerevisiae* YAP3 gene as a probe. A specific DNA fragment was identified, showing that, not only is the Yap3p proteolytic activity present in *P. angusta*, but a specific homologue of the YAP3 gene is present also.

The method of Southern hybridization used for detection of the YAP3 homologue can be adapted to clone the gene sequence from a genomic DNA library of Pichia DNA using standard procedures (Sambrook et al, 1989). Disruption of the YAP3 homologue in Pichia sp. can be achieved using similar techniques to those used above for Saccharomyces (Cregg and Madden, 1987).

REFERENCES (all incorporated by reference)

Azaryan, A. V. et al (1993) *J. Biol. Chem.* 268, 11968–11975.
Barnes, D. A. and Thorner, J. (1985) In Gene Manipulations in Fungi (Bennett,
J. W. and Lasure, L. L., eds), pp. 197–226, Academic Press.
Boeke, J. D. et al (1987) *Methods Enzymol.* 154, 164–175.
Botstein, D. et al (1979) *Gene* 8, 17–24.
Botstein & Shortle (1985) *Science* 229, 193–210.
Bourbonnais, Y. et al (1991) *J. Biol. Chem.* 266, 13203–13209.
Bourbonnais, Y. et al (1993) *EMBO J.* 12, 285–294.
Cawley, N. X. et al (1993) *FEBS Lett.* 332, 273–276.
Clerc et al (1994) *J. Chromat.* B. 662, 245–259.
Collins, S. H. (1990) In Protein Production by Biotechnology (Harris, T. J. R., ed) pp. 61–77, Elsevier Science Publishers, Barking, Essex.
Cregg, J. M. and Madden, K. R. (1987) In Biological Research on Industrial
Yeasts, Vol. II, Stewart, G. G., Russell, I., Klein, R. D. and Hiebsch, R. R. (Eds) CRC Press, Boca Raton, Fla.
Cregg et al (1993) *Bio/Technology* 11, 905–910.
Curling (1980) "Albumin Purification by Ion Exchange Chromatography", in "Methods of Plasma Protein Purification", Ed. Curling, J. M., Academic Press, London.
Enderlin, C. S. & Ogrydziak, D. M. (1994) *Yeast* 10, 67–79.
Fleer, R. et al (1991) *Bio/Technology* 9, 968–975.
Fuller, R. S. et al (1989) *Proc. Natl. Acad. Sci. USA* 86, 1434–1438.
Geisow, M. J. et al (1991) In Techniques in Protein Chemistry II, pp. 567–572,
Academic Press, Inc.
Gellissen et al (1992) *Tibtech* 10, 413–417.
Hoffmann & Winston (1990) *Genetics* 124, 807–816.
Maundrell (1990) *J. Biol. Chem.* 265, 10857–10864.
Maurel et al (1989) "Biotechnology of Plasma Proteins", *Colloque INSERM* 175, 19–24.
Romanos, M. A. (1992) *Yeast* 8, 423–488.
Rothstein, R. J. (1983) 1Methods Enzymol. 101, 203–211.
Sambrook, J. et al (1989) *Molecular Cloning a Laboratory Manual*, 2nd edition. Cold Spring Harbor Laboratory Press, Cold Spring Harbor, N.Y.
Sleep, D. et al (1990) *Bio/Technology* 8, 42–46.
Sleep, D. et al (1991) *Bio/Technology* 9, 183–187.
Tanguy-Rougeau, C. et al (1988) *FEBS Lett.* 234, 464–470
Wang, H. Y. et al (1979) *Biotech. & Bioeng.* 21, 975.
Winston, F. et al (1983) *Methods Enzymol.* 101, 211–228.

We claim:

1. A process for preparing albumin comprising: genetically modifying yeast cells having a reduced level of yeast aspartyl protease 3 proteolytic activity of at most 50% as compared to the corresponding activity level of naturally-occurring yeast cells of the same kind, to produce and secrete albumin, and culturing said yeast cells in a culture medium such that albumin is secreted into said culture medium.

2. The process of claim 1 wherein said albumin is a human albumin.

3. The process of claim 1 wherein said yeast cells are S. cerevisiae.

4. The process of claim 3 wherein said yeast cells also have a reduced level of S. cerevisiae Kex2p proteolytic activity of at most 50% of the wild type level.

5. The process of claim 1 wherein said yeast cells lack a functional YAP3 gene or homologue thereof, wherein said homoloque has YAP3p-like roteolytic activity.

6. The process of claim 1 wherein said proteolytic activity is an endoprotease activity specific for monobasic sites and for paired basic amino acids in a polypeptide.

7. The process of claim 6 wherein said yeast cells are S. cerevisiae.

8. The process of claim 7 wherein said yeast cells additionally have a reduced level of S. cerevisiae Kex2p proteolytic activity of at most 50% of the wild type level.

9. The process of claim 6 wherein said yeast cells lack a functional YAP3 gene or homologue thereof, wherein said homologue has YAP3p-like proteolytic activity.

10. A culture of yeast cells having a reduced level of yeast aspartyl protease 3 proteolytic activity of at most 50% as compared to the corresponding activity level of naturally-occurring yeast cells of the same kind, containing a polynucleotide sequence encoding an albumin and a second polynucleotide sequence encoding a secretion signal causing albumin expressed from the first polynucleotide sequence to be secreted from the yeast.

11. The culture of claim 10 wherein said albumin is a human albumin.

12. The culture of claim 10 wherein said yeast cells are *S. cerevisiae*.

13. The culture of claim 12 wherein said yeast cells have a reduced level of *S. cerevisiae* Kex2p proteolytic activity of at most 50% of the wild type level.

14. The culture of claim 10 wherein said yeast cells lack a functional YAP3 gene or homologue thereof, wherein said homologue has YAP3p-like proteolytic activity.

15. The culture of claim 10 wherein said yeast cells have a reduced level of Kex2p proteolytic activity of at most 50% of the wild type level.

16. The culture of claim 10 wherein said signal is cleaved by said yeast cells prior to release of said albumin from said yeast cells.

17. The culture of claim 15 wherein said secretion signal is cleaved from said albumin by a protease other than Kex2p.

18. A modified albumin, which when expressed and secreted in yeast is non-susceptible to cleavage with yeast aspartyl protease 3 (YAP3p).

19. The modified albumin of claim 18 wherein said modified albumin lacks a monobasic amino acid present in said naturally occurring albumin protein.

20. The modified albumin of claim 18 wherein the said monobasic amino acid is arginine.

21. The modified albumin of claim 19 wherein said modified albumin additionally lacks a pair of basic amino acids present in the naturally-occurring albumin.

22. The modified albumin of claim 21 wherein said pair of amino acids is Lys, Lys; Lys, Arg; Arg, Lys; or Arg, Arg.

23. The modified albumin of claim 18 wherein said naturally-occurring albumin is a human albumin and the modified albumin lacks $Arg^{410}$.

24. A modified albumin of claim 23 which is a human albumin having the amino acid changes R410A, K413Q, K414Q.

25. A polynucleotide encoding a modified albumin according to claim 18.

26. A yeast containing a polynucleotide according to claim 25 having transcription signals such that the modified albumin is expressed in the yeast, and a further polynucleotide adjacent the said polynucleotide such that said modified albumin is secreted from said yeast.

27. The modified albumin of claim 23 wherein residues 413 and 414 do not each consist of lysine or arginine.

\* \* \* \* \*